(12) United States Patent
Suh et al.

(10) Patent No.: US 8,815,267 B2
(45) Date of Patent: Aug. 26, 2014

(54) HYBRID POWDER OF HALLOYSITE NANOTUBE AND LIGHT-SCATTERING NANOPARTICLE, METHOD FOR PREPARING THE SAME, AND UV-SCREENING COSMETIC COMPOSITION CONTAINING THE SAME AS ACTIVE INGREDIENT

(76) Inventors: Yong Jae Suh, Daejeon (KR); Myung Eun Ju, Daejeon (KR); Dae Sup Kil, Daejeon (KR); Sung Wook Cho, Daejeon (KR)

( * ) Notice: Subject to any disclaimer, the term of this patent is extended or adjusted under 35 U.S.C. 154(b) by 0 days.

(21) Appl. No.: 13/266,263

(22) PCT Filed: Sep. 26, 2011

(86) PCT No.: PCT/KR2011/007064
§ 371 (c)(1),
(2), (4) Date: Apr. 12, 2012

(87) PCT Pub. No.: WO2013/047915
PCT Pub. Date: Apr. 4, 2013

(65) Prior Publication Data
US 2013/0078293 A1 Mar. 28, 2013

(51) Int. Cl.
*A61K 8/29* (2006.01)
*A61K 8/26* (2006.01)
*A61K 8/27* (2006.01)
*A61K 8/02* (2006.01)
*A61Q 17/04* (2006.01)
*B82Y 40/00* (2011.01)
*B82Y 30/00* (2011.01)

(52) U.S. Cl.
CPC ............. *A61K 8/26* (2013.01); *A61K 2800/412* (2013.01); *A61K 8/29* (2013.01); *A61Q 17/04* (2013.01); *A61K 8/0245* (2013.01); *B82Y 30/00* (2013.01); *Y10S 977/762* (2013.01); *Y10S 977/773* (2013.01); *Y10S 977/779* (2013.01); *Y10S 977/811* (2013.01); *Y10S 977/90* (2013.01); *Y10S 977/896* (2013.01); *Y10S 977/926* (2013.01)
USPC .............. 424/401; 424/489; 424/384; 424/59; 428/402; 977/762; 977/773; 977/779; 977/811; 977/900; 977/896; 977/926

(58) Field of Classification Search
USPC .................... 424/59, 401, 489; 428/384, 402; 977/762, 773, 779, 811, 900, 896, 926
See application file for complete search history.

(56) References Cited

U.S. PATENT DOCUMENTS

2003/0180535 A1* 9/2003 Horino et al. ................. 428/384
2007/0292459 A1 12/2007 Cooper et al.
2009/0022974 A1* 1/2009 Lee et al. .................... 428/304.4

FOREIGN PATENT DOCUMENTS

KR 1020070099960 A 4/2009

OTHER PUBLICATIONS

Lvov et al.: retrieved from internet: Halloysite Nanotubes, http://web.archive.org/web/20081030074326/http://www.sigmaaldrich.com/materials-science/nanomaterials/nanoclay-building/halloysite-nanotubes.html. Retrieved on Oct. 8, 2013.*
Horng: retrieved fom internet: Size-Controlled Synthesis and Hydrogenation of Anatase TiO2 Nanoparticles for Photocatalysis, www.rochester.edu/College/kearnscenter/pdf/.../Horng_Mike_Poster.pdf. Retrieved on Oct. 8, 2013.*
Applied Clay Science, vol. 50, Issue 1, Sep. 2010, pp. 118-124.

* cited by examiner

*Primary Examiner* — Ernst V Arnold
*Assistant Examiner* — Hong Yu
(74) *Attorney, Agent, or Firm* — Renner Kenner Greive Bobak Taylor & Weber (57) ABSTRACT

The present invention provides a hybrid powder of halloysite nanotubes and light-scattering nanoparticles, a method for preparing the same, and a UV-screening cosmetic composition containing the same as an active ingredient. The hybrid powder of halloysite nanotubes and light-scattering nanoparticles according to the present invention, in which the light-scattering nanoparticles are loaded into the halloysite nanotubes, can prevent the light-scattering nanoparticles from penetrating the skin, which minimizes side effects, and has excellent UV-screening effect. Thus, the hybrid powder of halloysite nanotubes and light-scattering nanoparticles according to the present invention can be effectively used as a UV-screening cosmetic composition.

1 Claim, 7 Drawing Sheets

HYBRID POWDER OF HALLOYSITE NANOTUBE AND LIGHT-SCATTERING NANOPARTICLE, METHOD FOR PREPARING THE SAME, AND UV-SCREENING COSMETIC COMPOSITION CONTAINING THE SAME AS ACTIVE INGREDIENT

TECHNICAL FIELD

The present invention relates to a hybrid powder of halloysite nanotubes and light-scattering nanoparticles, a method for preparing the same, and a UV-screening cosmetic composition containing the same as an active ingredient.

BACKGROUND ART

At present, it is known that titanium dioxide ($TiO_2$) nanoparticles, which are used as a main material of a UV-screening agent, have a better UV-screening effect when the size of the titanium dioxide nanoparticles is smaller. UV-screening ingredients are contained in commercially available skin care creams and lotions, makeup foundations, BB creams, and even in lip balms. However, when a lotion, for example, that contains titanium dioxide nanoparticles is rubbed on the skin burned by the sun or damaged by acne, the titanium dioxide nanoparticles may enter the human body through the skin to have harmful effects on the human body. Moreover, it is reported that the titanium dioxide nanoparticles are harmful materials to the human body through animal tests, and the National Institute for Occupational Safety and Health (NIOSH, USA) proposes a dose limit (0.1 $mg/m^2$).

Therefore, a method for reducing side effects, which may be caused by the titanium dioxide nanoparticles used as an active ingredient of the UV-screening agent, has attracted much attention.

Meanwhile, halloysite is a material represented by $Al_2Si_2O_5(OH)_4 \cdot 2H_2O$ and is an aluminum silicate clay mineral having a ratio of aluminum to silicon of 1:1. The halloysite is a nano-sized plate type and has a layer structure in which different layers are alternately layered in a ratio of 1:1. Moreover, the halloysite is naturally present in aluminosilicate. The outer surface of the halloysite comprises a silicate $SiO_2^-$ layer, and the inner surface comprises an alumina $Al_2O_3^+$ layer. The halloysite has a hollow nanotubular structure, in which the inner diameter is about 30 to 250 nm and the length is about 0.2 to 0.4 μm and thus has excellent carrier characteristics. Moreover, the halloysite is a natural mineral harmless to the human body, and thus there are no environmental problems and no harm to the human body. As a result, the nano-sized tubular halloysite has unique properties as a carrier and thus has been used as a container for an active substance, i.e., a carrier for delivering a fragrance, cosmetic, drug, etc.

However, it has not been reported that a hybrid powder in which light-scattering nanoparticles are loaded into halloysite nanotubes is developed.

Therefore, it is believed that when the light-scattering nanoparticles are loaded into halloysite nanotubes and used as an UV-screening agent, it is possible to reduce or eliminate side effects occurring on the skin. Thus, the need to develop a hybrid powder in which light-scattering nanoparticles are loaded into halloysite nanotubes is urgently required.

DISCLOSURE

Technical Problem

The inventors of the present invention have studied to discover a material having excellent UV-screening effect and minimizing side effects to the skin and have prepared a hybrid powder by loading light-scattering nanoparticles into halloysite nanotubes. As a result, the inventors of the present invention have confirmed that the UV-screening rate of the thus prepared hybrid powder is greater than that of pure halloysite and completed the present invention.

Therefore, the present invention provides a hybrid powder of halloysite nanotubes and light-scattering nanoparticles, a method for preparing the same, and a UV-screening cosmetic composition containing the same as an active ingredient.

Technical Solution

The present invention provides a hybrid powder of halloysite nanotubes and light-scattering nanoparticles, characterized in that the light-scattering nanoparticles are loaded into the halloysite nanotubes.

Moreover, the present invention provides a method for preparing a hybrid powder of halloysite nanotubes and light-scattering nanoparticles, comprising:

(1-1) preparing a colloidal solution by adding light-scattering nanoparticles to distilled water and dispersing the light-scattering nanoparticles by ultrasonic waves; and (1-2) adding a halloysite nanotube powder to the colloidal solution prepared in step (1-1), vacuum pulling the resulting solution, collecting a hybrid powder by centrifugation, and washing and drying the collected hybrid powder.

Furthermore, the present invention provides a method for preparing a hybrid powder of halloysite nanotubes and light-scattering nanoparticles, comprising:

(2-1) adding a halloysite nanotube powder to a light-scattering nanoparticle precursor solution or adding a light-scattering nanoparticle precursor solution and a halloysite nanotube powder to a hydrochloric acid solution, vacuum pulling the resulting solution, and collecting a hybrid powder by centrifugation; and (2-2) dispersing the hybrid powder collected in step (2-1) in a hydrochloric acid solution, stirring the resulting solution at 40 to 90° C. for 0.5 to 5 hours, cooling the resulting solution to room temperature, collecting the hybrid powder by centrifugation, and washing and drying the collected hybrid powder.

In addition, the present invention provides a UV-screening cosmetic composition containing a hybrid powder of halloysite nanotubes and light-scattering nanoparticles as an active ingredient.

Hereinafter, the present invention will be described in detail.

The hybrid powder of halloysite nanotubes and light-scattering nanoparticles according to the present invention is characterized in that the light-scattering nanoparticles are loaded into the halloysite nanotubes.

The light-scattering nanoparticles comprise at least one selected from the group consisting of, but not limited to, $TiO_2$, $ZnO$, $Fe_2O_3$, and $Fe_3O_4$.

The hybrid powder of halloysite nanotubes and light-scattering nanoparticles according to the present invention may be prepared by either of the following two methods.

The first method is a colloidal method of loading light-scattering nanoparticles directly into halloysite nanotubes. In detail, the light-scattering nanoparticles are added to distilled water and dispersed with ultrasonic waves to prepare a colloidal solution. Then, a halloysite nanotube powder is added to the colloidal solution and the resulting solution is vacuum pulled. Subsequently, a hybrid powder is collected by centrifugation, washed with a pH 1 solution and distilled water, and dried.

The second method is to produce light-scattering nanoparticles in halloysite nanotubes by immersing a light-scattering nanoparticle precursor material in halloysite nanotubes. In detail, a halloysite nanotube powder is added to a light-scattering nanoparticle precursor solution or a light-scattering nanoparticle precursor solution and a halloysite nanotube powder are added to a hydrochloric acid solution and the resulting solution is vacuum pulled. Subsequently, a hybrid powder is collected by centrifugation and washed with anhydrous ethanol. Then, the collected powder is dispersed in a hydrochloric acid solution, and the resulting solution is stirred at 40 to 90° C. for 0.5 to 5 hours, preferably at 60° C. for 3 hours and cooled to room temperature. Then, the hybrid powder is collected by centrifugation and washed with a pH 1 solution and distilled water, and dried.

Preferably, the light-scattering nanoparticle precursor material may comprise, but not limited to, titanium tetraisopropoxide (TTIP), zinc chloride ($ZnCl_2$), $FeCl_2$, and $FeCl_3$.

The hybrid powder of halloysite nanotubes and light-scattering nanoparticles prepared by the above method has a UV-screening rate higher than that of pure halloysite nanotubes. In particular, the hybrid powder prepared by a colloidal method has the highest UV-screening rate. It is believed that this is because the light-scattering nanoparticles are adsorbed onto the outer surface of the halloysite nanotubes as well as to the inside. Moreover, the hybrid powder has substantially the same UV-screening rate, regardless of the size of halloysite nanotubes.

As mentioned above, the hybrid powder of halloysite nanotubes and light-scattering nanoparticles according to the present invention, in which the light-scattering nanoparticles are loaded into the halloysite nanotubes, can prevent the light-scattering nanoparticles from penetrating the skin, which minimizes side effects, and has excellent UV-screening effect. Thus, the hybrid powder of halloysite nanotubes and light-scattering nanoparticles according to the present invention can be effectively used as a UV-screening cosmetic composition.

The cosmetic composition of the present invention may contain at least one known active ingredient having UV-screening activity.

Moreover, the cosmetic composition of the present invention may further comprise at least one cosmetically acceptable carrier other than the aforementioned active ingredients and may be incorporated into cosmetic formulations generally known in the art. In particular, the cosmetic composition of the present invention may contain lipids, organic solvents, dissolving agents, thickeners, gelling agents, softeners, antioxidants, suspending agents, stabilizers, foaming agents, fragrances, surfactants, water, ionic or nonionic emulsifiers, fillers, sequestering agents, chelating agents, preservatives, vitamins, UV-screening agents, humectants, essential oils, dyes, pigments, hydrophilic or lipophilic activators, liposomes, any other ingredients typically used in cosmetics, and supplements commonly used in the cosmetic field. Moreover, the cosmetic composition of the present invention may be formulated into a solution, suspension, emulsion, paste, gel, cream, lotion, powder, soap, surfactant-containing cleansing oil, powder foundation, emulsion foundation, wax foundation, and spray, but not limited thereto. More specifically, the cosmetic composition of the present invention may be formulated into a softening lotion, nutrient lotion, milk lotion, nutrient cream, massage cream, essence, eye cream, cleansing cream, cleansing foam, cleansing water, pack, spray, or powder.

In the cosmetic composition of the present invention, the hybrid powder of halloysite nanotubes and light-scattering nanoparticles may be contained in an amount of 0.01 to 25 wt %, preferably 0.1 to 5 wt % with respect to the total weight of the cosmetic composition. If the content of the hybrid powder of halloysite nanotubes and light-scattering nanoparticles is less than 0.01 wt %, the UV-screening effect cannot be expected, whereas, if it exceeds 25 wt %, it may cause irritation to the skin and have a significant effect on the stabilization of the formulation.

Advantageous Effects

The hybrid powder of halloysite nanotubes and light-scattering nanoparticles according to the present invention, in which the light-scattering nanoparticles are loaded into the halloysite nanotubes, can prevent the light-scattering nanoparticles from penetrating the skin, which minimizes side effects, and has excellent UV-screening effect.

MODE FOR INVENTION

Hereinafter, preferred examples will be presented for a better understanding of the present invention. It is to be understood, however, that these examples are provided for illustrative purpose only and are not to be construed to limit the scope of the present invention.

EXAMPLE 1

Preparation of Hybrid Powder of Halloysite Nanotubes and Titanium Dioxide Nanoparticles by Colloidal Method The colloidal method was used to load titanium dioxide nanoparticles, which were prepared separately, directly into halloysite nanotubes.

In detail, while a 1M HCl (80 ml) was placed in a 250 ml beaker and stirred using a magnetic bar, titanium tetraisopropoxide (TTIP) (20 ml) was slowly added thereto and then stirred at 60° C. for 3 hours. When titanium dioxide nanoparticles were produced, the temperature of the solution was lowered to room temperature, and the titanium dioxide nanoparticles were collected by centrifugation (at 10,000 rpm for 3 minutes). The collected titanium dioxide nanoparticles were added to distilled water (20 ml) and dispersed with ultrasonic waves for 30 minutes to prepare a colloidal solution. Then, a halloysite nanotube powder (3 g) was added to the colloidal solution and the resulting solution was vacuum pulled. Subsequently, a hybrid powder was collected by centrifugation, washed with a pH 1 solution twice and distilled water once, and dried at 60° C.

EXAMPLE 2

Preparation of Hybrid Powder of Halloysite Nanotubes and Titanium Dioxide Nanoparticles by TTIP Solution Method The TTIP solution method was used to load titanium dioxide nanoparticles into halloysite nanotubes by immersing halloysite nanotubes in a TTIP solution and then immersing the resulting halloysite nanotubes in an HCL solution.

In detail, a halloysite nanotube powder (3 g) was added to a TTIP solution (20 ml) and the resulting solution was vacuum pulled. Then, a powder was collected by centrifugation and washed with anhydrous ethanol once. Then, the collected powder was dispersed in a 1M HCl solution (80 ml), and the resulting solution was stirred at 60° C. for 3 hours. The resulting solution was cooled to room temperature, and a hybrid powder was collected by centrifugation and washed with a pH 1 solution once and distilled water once, and dried at 60° C.

EXAMPLE 3

Preparation of Hybrid Powder of Halloysite Nanotubes and Titanium Dioxide Nanoparticles by TTIP-HCL Solution Method The TTIP-HCL solution method was used to load titanium dioxide nanoparticles into halloysite nanotubes by adding halloysite nanotubes during synthesis of titanium dioxide nanoparticles.

In detail, a TTIP solution (20 ml) was added to a 1M HCl solution (80 ml) and stirred at 60° C. A halloysite nanotube powder (3 g) was added to the resulting solution after 30 minutes and then vacuum pulled. Subsequently, a powder was collected by centrifugation and washed with anhydrous ethanol once. Then, the collected powder was dispersed in a 1M HCl solution (80 ml), and the resulting solution was stirred at 60° C. for 3 hours. The resulting solution was cooled to room temperature, and a hybrid powder was collected by centrifugation and washed with a pH 1 solution once and distilled water once, and dried at 60° C.

EXPERIMENTAL EXAMPLE 1

Measurement of UV-screening Rate of Hybrid Powder of Halloysite Nanotubes and Titanium Dioxide Nanoparticles According to Present Invention The following experiment was performed to calculate the UV-screening rate of the hybrid powder of halloysite nanotubes and titanium dioxide nanoparticles according to the present invention.

In detail, the hybrid powders of halloysite nanotubes and titanium dioxide nanoparticles prepared in Examples 1 to 3 were added to distilled water and diluted to 0.0025 wt %, thus preparing measurement samples. The measurement samples were injected into a 1-cm path length quartz cuvette and mounted in a spectrometer. Then, the light transmittances of the samples were measured in a wavelength range of 250 to 500 nm using a UV/Vis spectrometer (Scinco S3100, Korea). The absorbances of the samples were calculated from the measured light transmittances by the following formula I based on the Beer-Lambert law. When the concentration of nanoparticles and the path length are constant, the absorbance (A) is proportional to the extinction coefficient ($\epsilon$), and thus it is possible to quantitatively compare the extinction coefficients of the samples.

Moreover, the entire UV-screening rates were obtained by integrating the UV-screening rates of the hybrid powders of halloysite nanotubes and titanium dioxide nanoparticles prepared in Examples 1 to 3 in the UV wavelength range (UV-B, UV-A).

$$A = \epsilon c l = -\log(I/I_0) \qquad \text{[Formula 1]}$$

In formula 1, A represents the absorbance, $\epsilon$ represents the extinction coefficient, c represents the concentration of nanoparticles, l represents the path length of light passing through the sample, $I_0$ represents the initial intensity of light, I represents the intensity of light transmitted through the sample, and $I/I_0$ represents the transmittance.

Figure 1:
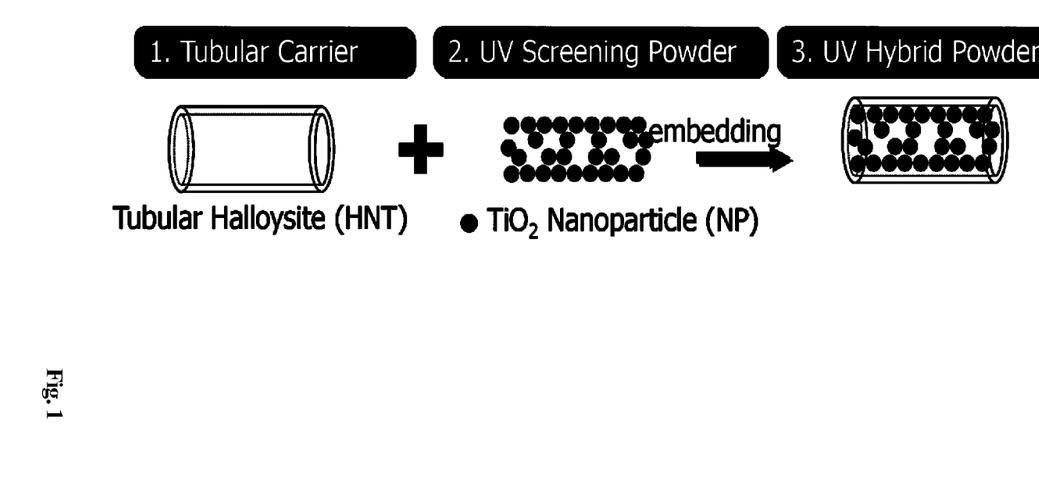
FIG. 1 is a schematic diagram showing a hybrid powder of halloysite nanotubes and light-scattering nanoparticles according to the present invention.
Figure 2:
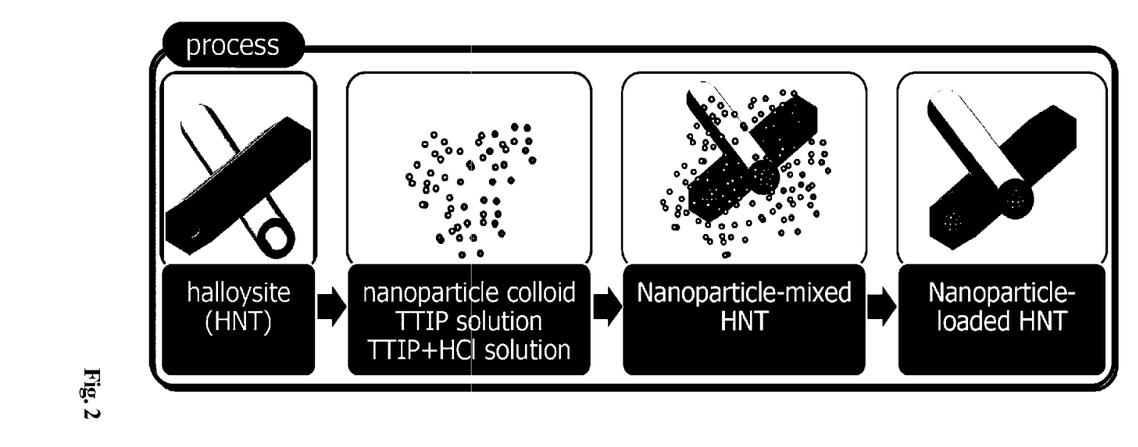
FIG. 2 is a schematic diagram showing a method for preparing a hybrid powder of halloysite nanotubes and light-scattering nanoparticles according to the present invention.
Figure 3:
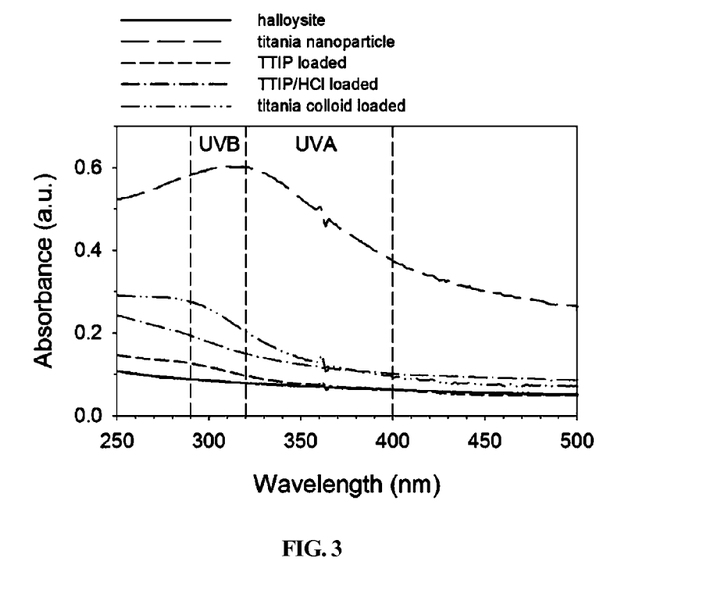
FIG. 3 is a graph showing the UV-screening rate of the hybrid powder of halloysite nanotubes and titanium dioxide nanoparticles according to the present invention.
Figure 4:
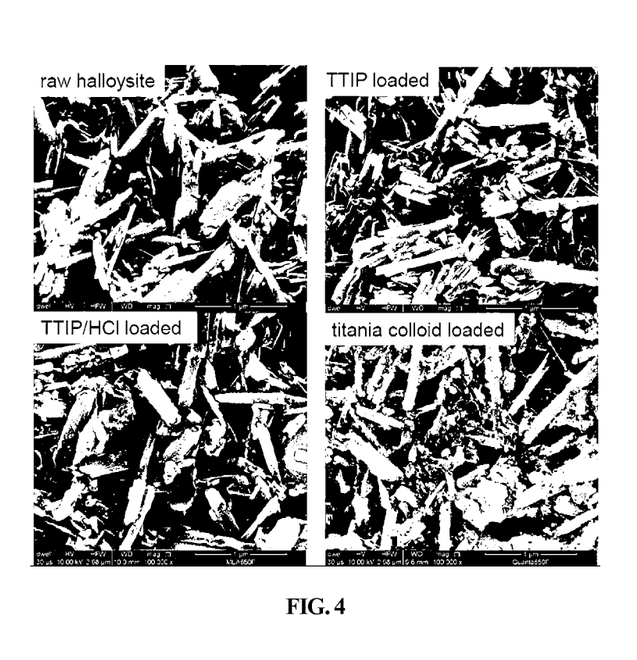
FIG. 4 shows the results of scanning electron microscope (SEM) observation of the hybrid powder of halloysite nanotubes and titanium dioxide nanoparticles according to the present invention.
Figure 5:
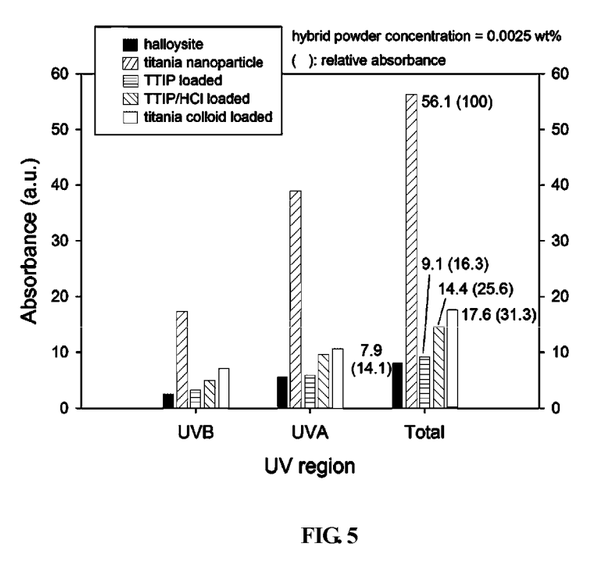
FIG. 5 is a graph showing the entire UV-screening rate obtained by integrating the UV-screening rate of the hybrid powder of halloysite nanotubes and titanium dioxide nanoparticles according to the present invention in the UV wavelength range (UV-B, UV-A)

The UV-screening rates and the results of scanning electron microscope (SEM) observation of the hybrid powder of halloysite nanotubes and titanium dioxide nanoparticles according to the present invention are shown in FIGS. 3 and 4, respectively, the entire UV-screening rates obtained by integrating the UV-screening rate of the hybrid powder of halloysite nanotubes and titanium dioxide nanoparticles according to the present invention in the UV wavelength range (UV-B, UV-A) is shown in FIG. 5.

As shown in FIGS. 3 and 4, in the case of the hybrid powder prepared by loading titanium dioxide nanoparticles directly into halloysite nanotubes using the colloidal method (Example 1), the UV-screening rate was ranked first, compared to pure halloysite nanotubes. Then, the UV-screening rate was ranked second in the case of the hybrid powder prepared by loading titanium dioxide nanoparticles into halloysite nanotubes using both TTIP and HCL solution by the TTIP-HCL solution method (Example 3) and then ranked third in the case of the hybrid powder prepared by the TTIP solution method (Example 2). It is believed that this is because the titanium dioxide nanoparticles were adsorbed onto the outer surface of the halloysite nanotubes as well as to the inside when the colloidal method was used and the hydrolysis reaction proceeded more efficiently when the TTIP-HCl solution method was used, compared to the TTIP solution method.

Moreover, as shown in FIG. 5, the hybrid powder prepared by loading titanium dioxide nanoparticles directly into halloysite nanotubes using the colloidal method (Example 1) showed a UV-screening rate (A=17.6) improved by 17.2% across the entire UV region, compared to pure halloysite nanotubes. This means that when the concentration of the hybrid colloidal solution is increased 3.2 times (0.008 wt %), it is possible to obtain the same UV-screening rate (A=56.1) as the colloidal solution (0.0025 wt %) containing only the titanium dioxide nanoparticles.

EXPERIMENTAL EXAMPLE 2

Measurement of UV-Screening Rate of Hybrid Powder of Halloysite Nanotubes and Titanium Dioxide Nanoparticles According to Size Distribution of Halloysite Nanotubes Hybrid powders of halloysite nanotubes and titanium dioxide nanoparticles were prepared using (a) mixed halloysite nanotubes, (b) fine halloysite nanotubes of 0.2 to 1.0 μm in size, and (c) coarse halloysite nanotubes of 1.0 to 8.0 μm in size using the colloidal method in Example 1. The UV-screening rates of the prepared hybrid powders were measured in the same manner as in Experimental Example 1.

Figure 6:
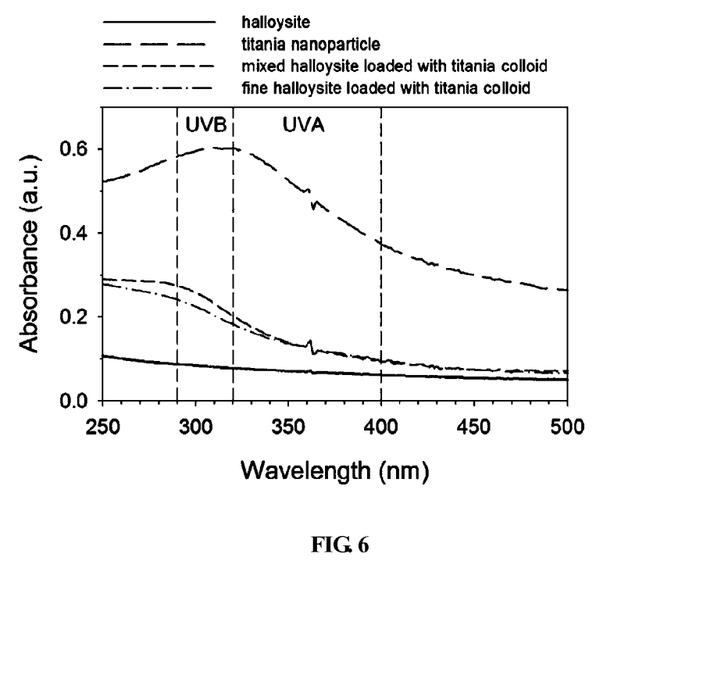
FIG. 6 is a graph showing the UV-screening rates of the hybrid powders of halloysite nanotubes and titanium dioxide nanoparticles according to the size distribution of halloysite nanotubes.
Figure 7:
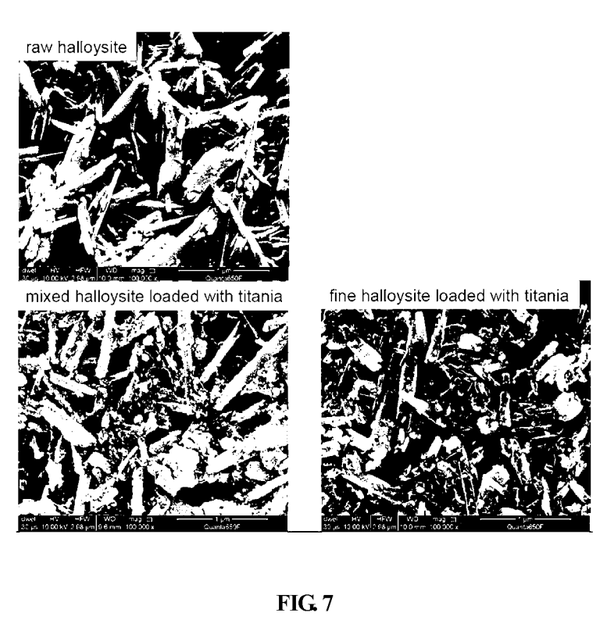
FIG. 7 shows the results of SEM observation of the hybrid powders of halloysite nanotubes and titanium dioxide nanoparticles according to the size distribution of halloysite nanotubes.

The UV-screening rates and the results of SEM observation of the hybrid powders of halloysite nanotubes and titanium dioxide nanoparticles according to the size distribution of halloysite nanotubes are shown in FIGS. 6 and 7, respectively.

As shown in FIGS. 6 and 7, the UV-screening rates of the hybrid powders were substantially the same, regardless of the size of halloysite nanotubes. It is believed that this is because, in the case of the coarse halloysite nanotubes of 1.0 to 8.0 μm in size, the titanium dioxide nanoparticles loaded into the halloysite nanotubes were separated from the halloysite nanotubes and adsorbed onto the outer surface of the halloysite nanotubes during the washing process.

Preparation examples for the cosmetic compositions of the present invention will be described below.

PREPARATION EXAMPLE 1

Preparation of Softening Lotion

TABLE 1

| Ingredients | Content (wt %) |
|---|---|
| Hybrid powder of halloysite nanotubes and titanium dioxide nanoparticles | 0.5 |
| 1,3-butylene glycol | 5.2 |
| Oleyl alcohol | 1.5 |
| Ethanol | 3.2 |
| Polysorbate 20 | 3.2 |
| Benzophenone-9 | 2.0 |
| Carboxyvinyl polymer | 1.0 |
| Glycerin | 3.5 |
| Fragrance | Small quantity |
| Preservative | Small quantity |
| Purified water | Residual quantity |
| Total | 100 |

Softening lotion was prepared by mixing the above ingredients by a usual preparation method.

PREPARATION EXAMPLE 2

Preparation of Milk Lotion

TABLE 2

| Ingredients | Content (wt %) |
|---|---|
| Hybrid powder of halloysite nanotubes and titanium dioxide nanoparticles | 0.6 |
| Glycerin | 5.1 |
| Propylene glycol | 4.2 |
| Tocopheryl acetate | 3.0 |
| Liquid paraffin | 4.6 |
| Triethanolamine | 1.0 |
| Squalane | 3.1 |
| Macadamia nut oil | 2.5 |
| Polysorbate 60 | 1.6 |
| Sorbitan sesquioleate | 1.6 |
| Propylparaben | 0.6 |
| Carboxyvinyl polymer | 1.5 |
| Fragrance | Small quantity |
| Preservative | Small quantity |
| Purified water | Residual quantity |
| Total | 100 |

Milk lotion was prepared by mixing the above ingredients by a usual preparation method.

PREPARATION EXAMPLE 3

Preparation of Nutrient Cream

TABLE 3

| Ingredients | Content (wt %) |
|---|---|
| Hybrid powder of halloysite nanotubes and titanium dioxide nanoparticles | 1.0 |
| Glycerin | 4.0 |
| Vaseline | 3.5 |
| Triethanolamine | 2.1 |
| Liquid paraffin | 5.3 |
| Squalane | 3.0 |
| Wax | 2.6 |
| Tocopheryl acetate | 5.4 |
| Polysorbate 60 | 3.2 |
| Carboxyvinyl polymer | 1.0 |
| Sorbitan sesquioleate | 3.1 |
| Fragrance | Small quantity |
| Preservative | Small quantity |
| Purified water | Residual quantity |
| Total | 100 |

Nutrient cream was prepared by mixing the above ingredients by a usual preparation method.

The invention claimed is:

1. A method for preparing a hybrid powder of halloysite nanotubes and $TiO_2$ light-scattering nanoparticles, comprising:
   (2-1) adding a halloysite nanotube powder to titanium tetraisopropoxide (TTIP) solution, vacuum pulling the resulting solution, and collecting a hybrid powder by centrifugation; and
   (2-2) dispersing the hybrid powder collected in step (2-1) in a hydrochloric acid solution, stirring the resulting solution at 40 to 90° C. for 0.5 to 5 hours, cooling the resulting solution to room temperature, collecting the hybrid powder by centrifugation, and washing and drying the collected hybrid powder.

* * * * *